(12) United States Patent
Palmer, Jr. et al.

(10) Patent No.: US 9,644,108 B2
(45) Date of Patent: May 9, 2017

(54) ADDITIVES TO IMPROVE OPEN-TIME AND FREEZE-THAW CHARACTERISTICS OF WATER-BASED PAINTS AND COATINGS

(71) Applicant: Ethox Chemicals, LLC, Greenville, SC (US)

(72) Inventors: Charles F. Palmer, Jr., Greenville, SC (US); Lester Arnold Haney, Greenville, SC (US); Calvin M. Wicker, Jr., Greenville, SC (US)

(73) Assignee: Ethox Chemicals, LLC, Greenville, SC (US)

( * ) Notice: Subject to any disclaimer, the term of this patent is extended or adjusted under 35 U.S.C. 154(b) by 0 days.

(21) Appl. No.: 15/093,355

(22) Filed: Apr. 7, 2016

(65) Prior Publication Data

US 2016/0222243 A1    Aug. 4, 2016

Related U.S. Application Data

(63) Continuation-in-part of application No. 13/792,175, filed on Mar. 10, 2013, now Pat. No. 9,309,376.

(60) Provisional application No. 61/609,269, filed on Mar. 10, 2012.

(51) Int. Cl.
| | |
|---|---|
| C08K 5/06 | (2006.01) |
| C09D 113/02 | (2006.01) |
| C07F 9/11 | (2006.01) |
| C08K 5/098 | (2006.01) |
| C08G 65/02 | (2006.01) |
| C08G 65/14 | (2006.01) |
| C08G 65/22 | (2006.01) |
| C08G 65/26 | (2006.01) |
| C08G 65/326 | (2006.01) |
| C08G 65/331 | (2006.01) |
| C09D 171/02 | (2006.01) |
| C08K 5/41 | (2006.01) |
| C08K 5/52 | (2006.01) |
| C08L 71/02 | (2006.01) |
| C08G 65/327 | (2006.01) |

(52) U.S. Cl.
CPC .............. *C09D 113/02* (2013.01); *C07F 9/11* (2013.01); *C08G 65/02* (2013.01); *C08G 65/14* (2013.01); *C08G 65/22* (2013.01); *C08G 65/2612* (2013.01); *C08G 65/326* (2013.01); *C08G 65/327* (2013.01); *C08G 65/331* (2013.01); *C08K 5/06* (2013.01); *C08K 5/098* (2013.01); *C08K 5/41* (2013.01); *C08K 5/52* (2013.01); *C08L 71/02* (2013.01); *C09D 171/02* (2013.01)

(58) Field of Classification Search
CPC .................................................... C09D 113/02
USPC .......................................................... 524/366
See application file for complete search history.

(56) References Cited

U.S. PATENT DOCUMENTS

2007/0072983 A1* 3/2007 Watanabe ................. C08F 2/30
524/459

* cited by examiner

*Primary Examiner* — Hui Chin
(74) *Attorney, Agent, or Firm* — Joseph T. Guy; Perkins Law Firm, LLC

(57) ABSTRACT

Waterborne coatings are described having an acceptable balance of properties both during the storage of coating, application and drying. The period in which irregularities in a freshly applied coating can be repaired without resulting in brush marks is referred to as the open time. Aqueous coatings generally employ dispersed high molecular weight polymers as binders. These binders often provide short open times when the coating is dried since the dispersed polymer particles tend to be immobilized quickly in the edge region of an applied coating. As a result, the viscosity of the coating increases rapidly, which leads to a limited window of workability. The instant invention provides additives that are not volatile but that will extend the time that the film is malleable after it is applied without interfering with other attributes, such as the resistance of the coating to freezing while in the can prior to application.

8 Claims, No Drawings

ADDITIVES TO IMPROVE OPEN-TIME AND FREEZE-THAW CHARACTERISTICS OF WATER-BASED PAINTS AND COATINGS

CROSS-REFERENCE TO RELATED APPLICATIONS

This application is a Continuation-in-Part application of U.S. patent application Ser. No. 13/792,175 filed Mar. 10, 2013 which, in turn, claims the priority benefit under 35 U.S.C. section 119 of U.S. Provisional Patent Application No. 61/609,269 filed on Mar. 10, 2012; both of which are entirety herein incorporated by reference.

FIELD OF THE INVENTION

The present invention relates to the use of a particular family of alkoxylated compounds and allylglycidy ether derivatives thereof for improving open time characteristics of aqueous coating compositions such as paints, alkyd paints, inks and other paper coating compositions.

More specifically, this invention is directed to the use of various agents as additives to increase the open time and improve the freeze-thaw stability of water-based latex paint coatings. The agents found to cause such improvements were: Tristyrenated phenols reacted with one or two units of allylglycidyl ether, then ethylene oxide, then possibly sulfamic acid to yield an anion, Distyrenated phenols reacted with one or two units of allylglycidyl ether and then ethylene oxide, Ethoxylated beta naphthol, Dodecyl benzene sulfonic acid neutralized with triethanolamine and formulated with a reverse ethylene oxide/propylene oxide reverse block co-polymer and water.

BACKGROUND

Waterborne paints, inks, and other coatings are used for a multitude of applications including interior and exterior coatings for paper, wood, architectural surfaces, and many more. These coatings are composed of a number of components such as latex, alkyd, or other binders, pigments or other colorants, water, coalescing agents, thickeners, solvents, and a number of surfactants for various purposes. With strict environmental legislation requiring the reduction of the amount of Volatile Organic Compounds (VOC) in coatings, it is desirable to have paint formulations with little or no VOC content. Common VOC components in paint include coalescing agents and glycol freeze-thaw stability additives, among others. Removing these has resulted in a number of formulation and composition challenges. However, due to competitive pressures, low VOC coatings and paints must maintain or exceed coating performance standards expected in the industry.

Since waterborne coatings are subject to freezing at low temperatures commonly experienced in shipping or storage in northern latitudes, there is significant interest in improving the freeze/thaw stability of latex paints. As a consequence of reducing or eliminating VOCs in latex paints due to government regulations, simple glycols such as propylene glycol (PG), commonly used to help improve freeze/thaw stability, are being eliminated. Many coalescing solvents such as Texanol (IBT) that are VOCs are also being eliminated requiring softer (lower Tg) latexes to be used instead of the traditional harder (high Tg) latexes. Softer latexes have poorer freeze/thaw stability characteristics than higher Tg latexes further increasing the need for non-VOC freeze/thaw stability additives.

For low VOC paint binder latexes, the average Tg is close to or below 0° C. so that little or no coalescent is needed to make a good coating after drying. However, latex binders with low Tg often cause grit when subjected to freeze/thaw cycles as well as exposure to mechanical shear. The resulting coating films are softer and tackier, even after fully dried, and are susceptible to blocking and dirt pick-up effects. Also, such low Tg latex binders and resulting latex paints are not stable, and gel in a cold environmental storage or transportation process. Freeze-thaw stability of low Tg latex binders and low VOC paints is critically important for transportation, storage, and practical applications. Thus, there is a need to develop latex paints and latex particle dispersions that meet zero or low VOC requirements and at the same provide excellent mechanical and film performance without sacrificing the freeze-thaw stability of those paints. This requires non-VOC freeze/thaw stability additives.

In traditional latex binders for architectural coatings, the glass transition temperature is between about 10° C. to about 40° C. These higher Tg latexes do not suffer from the grit, blocking, and other problems that the low Tg latexes do. However, architectural coating formulations based on them usually need coalescent agents and anti-freeze agents, both of which are typically high-VOC solvents. Thus, there is a need for non-VOC freeze/thaw stability additives for use with higher Tg latex binders.

Latex freeze-thaw (sometimes herein referred to as "F/T") stability, including the freezing-thawing process, destabilization mechanism, and polymer structures, have been extensively studied since 1950. Blackley, D. C., Polymer Lattices-Science and Technology, $2^{nd}$ Ed., Vol. 1, Chapman & Hall, 1997, gives a comprehensive review of colloidal destabilization of latexes by freezing. The freezing process starts with the decrease of temperature, which leads to the formation of ice crystals. The ice crystal structures progressively increase the latex particle concentration in the unfrozen water. Eventually latex particles are forced into contact with each other as the pressure of growing ice crystal structures, resulting in particle aggregation or interparticle coalescence.

To make a stable latex dispersion in aqueous medium or latex paints with freeze-thaw stability, various approaches have been employed. The addition of antifreeze agents, e.g. glycol derivatives, has been applied to latex paint to achieve freeze-thaw stability. Thus, latex paints include anti-freeze agents to allow the paints to be used even after they have been subjected to freezing conditions. Exemplary anti-freeze agents include ethylene glycol, diethylene glycol, and propylene glycol. For a more detailed discussion see Bosen, S. F., Bowles, W. A., Ford, E. A., and Person, B. D., "Anti-freezes," Ullmann's Encyclopedia of Industrial Chemistry, $5^{th}$ Ed., Vol. A3, VCH Verlag, pages 23-32, 1985. However, since these simple glycols are VOCs, a low or no VOC requirement for the formulated paint means that the glycol level has to be reduced or eliminated.

A number of methods to achieve freeze/thaw stability are known in the art. Farwaha et. al. (U.S. Pat. No. 5,399,617) discloses the use of copolymerizable amphoteric surfactants and discloses latex copolymers comprising the copolymerizable amphoteric surfactants to impart freeze-thaw stability to the latex paints. Zhao et. al. (U.S. Pat. No. 6,933,415 B2) discloses latex polymers including polymerizable alkoxylated surfactants and discloses the low VOC aqueous coatings based on them have excellent freeze-thaw stability. Farwaha et. al. (U.S. Pat. No. 5,610,225) discloses incorporating a monomer with long polyethylene glycol structures to achieve stable freeze-thaw latex. Okubo et. al. (U.S. Pat.

No. 6,410,655 B2) discloses freeze-thaw stability of latex polymers including ethylenic unsaturated monomers.

It is well known that certain nonionic surfactants impart varying degrees of freeze/thaw stability to latexes; however, the levels required to impart freeze/thaw stability vary as a function of the Tg of the polymers and the propylene glycol level. Some of these nonionic surfactants are disclosed in U.S. Pat. No. 7,906,577 and in U.S. Pat. No. 8,304,479. Some of these can also function as open time extenders.

Another one of the challenges of formulating waterborne coatings is achieving an acceptable balance of properties both during the film application and drying process as well as in the final film. There is a competition between the requirements for adequate workability time of the coating with appropriate film formation and recoat behavior. The period in which irregularities in a freshly applied coating can be repaired without resulting in brush marks is referred to as the open time, while the period in which a coating can be applied over an existing paint film without leaving lap marks is deemed the wet edge time.

Aqueous coatings generally employ dispersed high molecular weight polymers as binders. These binders often provide short open times when the coating is dried since the dispersed polymer particles tend to be immobilized quickly in the edge region of an applied coating. As a result, the viscosity of the coating increases rapidly, which leads to a limited window of workability. Small molecule alkylene glycols such as ethylene and propylene glycol are routinely incorporated in aqueous coatings as humectants, but are considered to be VOCs. Thus, there is also a need for low VOC additives to improve open time and wet edge in aqueous coatings.

As mentioned above, surfactants are common components of waterborne coating formulations. They have many functions including dispersing pigments, wetting the substrate, improving flow and leveling, etc. However, once the coating has been applied to a substrate the surfactant is no longer needed. In fact, the presence of the surfactant often degrades the moisture sensitivity of the coating. Other coating properties can be negatively affected as well. This is largely due to the mobility of the surfactant polymers. For example, locally high concentrations of surfactant molecules can form in the coating from the coalescence of surfactant-coated micelle spheres. When the coating is exposed to water, these unbound surfactant molecules can be extracted from the coating leaving thin spots or pathways to the substrate surface. This can result in "blushing" and corrosion of the substrate.

Since surfactants have a number of deleterious effects on the finished coating and add cost to the coating formulation, minimizing their use would be desirable. A non-VOC additive that had multiple functions in the formulation such as imparting freeze/thaw stability, and extending open time and wet edge, and improving coalescence, could reduce the cost of and improve the performance of the finished coating.

The present invention provides alkoxylated styrenated phenols and naphthols that have been derivatized with allyl glycidyl ether as additives to impart WE/OT to Semigloss paints. Note that the study was done with acrylic latexes. Different results may be obtained with Vinyl Acrylic or Vinyl Acetate Ethylene (VAE) latexes since they are more hydrophilic. The "Martha Stewart Paint was a vinyl acrylic according to the label. Glidden has manufactured the paint under the Martha Stewart label until last year. Now, they still manufacture that paint but under the Glidden Interior Premium Paint (Semigloss) label. The Martha Stewart colors still work with the paint since it identical to the paint made in the past.

SUMMARY OF THE INVENTION

The invention relates to a coating composition comprising: (a) at least one latex polymer; (b) water; and (c) at least one open time and freeze-thaw additive in an amount effective to increase the open time and freeze thaw properties of the coating composition the additive having the structural formula

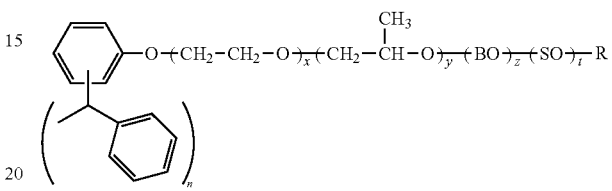

where n=2, x=10-12, y=0-10, z=0-10 and t=0-10, BO denotes a moiety derived from butylene oxide and SO denotes a moiety derived from styrene oxide and R is hydrogen or a
$C_1$-$C_{22}$ alkyl group and wherein the additive is present in an amount greater than about 0.5% by weight of the polymer.

The invention also provides a coating composition comprising: (a) at least one latex polymer; (b) water; and (c) at least one open time and freeze-thaw additive in an amount effective to increase the open time and freeze thaw properties of the coating composition the additive having the structural formula

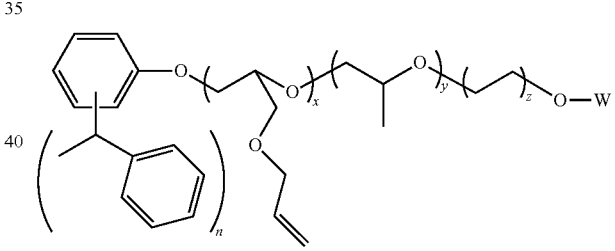

where n=1-3, x=1-5, y=0-10, z=5-40, W is selected from the group consisting of hydrogen and $1M^+$ where Z is selected from the group consisting of $SO_3^-$ and $PO_3^{2-}$, and $M^+$ is selected from the group consisting of $Na^+$, $K^+$, $NH_4^+$, or an alkanolamine; and wherein the additive is present in an amount greater than about 0.5% by weight of the polymer.

It is believed that the present invention in part stabilizes the latex particles using steric effects of larger hydrophobic groups to form a protective layer on the surfaces of soft latex particles. The large hydrophobic groups adsorbed or grafted onto the latex particles or co-polymerized into the latex particles prevent these latex particles from approaching the surfaces of other soft latex particles and increase the distance of separation between soft latex particles. The alkylene, e.g., ethylene oxide units from the surfactant of the alkoxylated compounds chains also form a layer which interacts with the aqueous medium.

DESCRIPTION

The instant invention is directed to a coating composition comprising: (a) at least one latex polymer; (b) water; and (c)

at least one open time and freeze-thaw additive in an amount effective to increase the open time and freeze thaw properties of the coating composition the additive having the structural formula I:

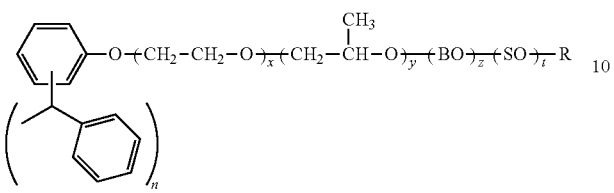

where n=2, x=10-12, y=0-10, z=0-10 and t=0-10, BO denotes a moiety derived from butylene oxide and SO denotes a moiety derived from styrene oxide and R is hydrogen or a $C_1$-$C_{22}$ alkyl group and wherein the additive is present in an amount greater than about 0.5% by weight of the polymer.

The invention is further directed to a coating composition comprising: (a) at least one latex polymer; (b) water; and (c) at least one open time and freeze-thaw additive in an amount effective to increase the open time and freeze thaw properties of the coating composition the additive having the structural formula II:

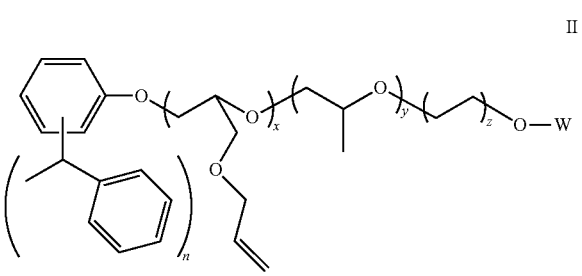

where n=1-3, x=1-5, y=0-10, z=5-40, W is selected from the group consisting of hydrogen and $1M^+$ where Z is selected from the group consisting of $SO_3^-$ and $PO_3^{2-}$, and $M^+$ is selected from the group consisting of $Na^+$, $K^+$, $NH_4^+$, or an alkanolamine; and wherein the additive is present in an amount greater than about 0.5% by weight of the polymer. Preferably, x=1-3 and more preferably x=1-2.

This compounds of formula I and II provide improvements in water-based latex paints. More specifically, the improvements are (1) the increase of the open time of water based latex paints and (2) the increase in the number of times that the paint can be frozen and then thawed before it loses it integrity as a uniform dispersion.

Additional compounds which are useful in providing improved properties to the coating compositions of the invention are selected from the group consisting of:

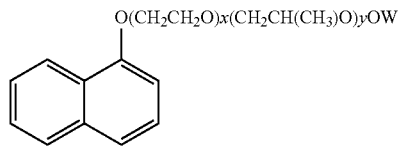

POE 10 β-naphthol

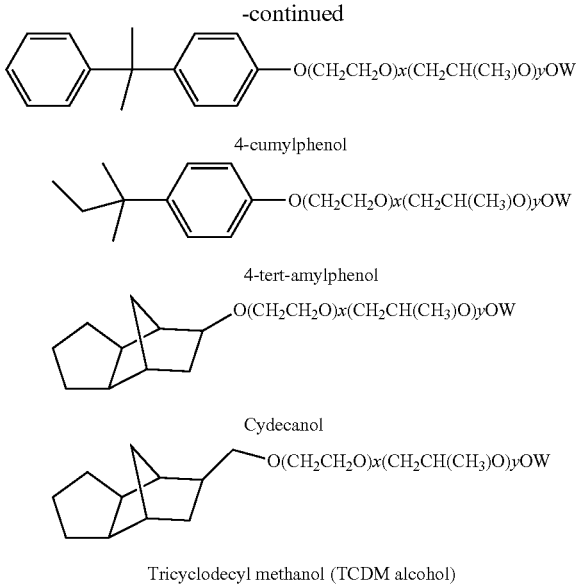

Tricyclodecyl methanol (TCDM alcohol)

where x=5-40 preferably is x=10; y=0-10, preferably is y=0; W is selected from the group consisting of H, sulfate ($—SO_3^-M^+$), phosphate ($—PO_3H^-(M)$) and carboxylate ($OCH_2COO^-M^+$) where $M^+$ is selected from the group consisting of $Na^+$, $K^+$, $NH_4^+$ and triethanolamine.

The compounds of the invention can be used in a number of ways for improving open time characteristics, freeze-thaw cycles, as well as drying time characteristics, of latex binders, paints, inks and other coatings. The present invention may optionally employ polymerizable reactive alkoxylated monomers as a reactant during emulsion polymerization to form the latex polymer. The present invention may employ one or more surface active alkoxylated compounds of the formula I or II as a surfactant (e.g., emulsifier) during emulsion polymerization to form the latex polymer. The present invention also uses compounds of the formula I or II as an additive to latex polymer-containing formulations such as coatings, including but not limited to paints; as well as an additive for adhesives, including but not limited to pressure sensitive adhesives; glues; resins; sealants; inks, including but not limited to UV inks, conventional inks, hybrid inks, and water-based inks; and the like.

The invention also provides a latex paint composition which is freeze-thaw stable with improved open time, wet edge time and drying time characteristics.

In an alternate embodiment, the latex coating composition contains an open time additive in an amount effective to lengthen the open time of the composition to greater than 4 minutes, typically greater than 6 minutes. In one embodiment, improved open time characteristics means that the open time of a coating or adhesive is made greater than 4 minutes. In another embodiment, improved open time characteristics means that the open time of a coating or adhesive is made greater than 6 minutes. In a further embodiment, improved open time characteristics means that the open time of a coating or adhesive is made greater than 8 minutes. In another embodiment, improved open time characteristics means that the open time of a coating or adhesive is made greater than 10 minutes. In alternate embodiment, improved open time characteristics means that the open time of a coating or adhesive is made greater than 12 minutes.

The coating compositions of the invention can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, biocides, mildewcides, colorants such as colored pigments and dyes, waxes, perfumes, co-solvents, and the like, can also be used in accordance with the invention.

The aqueous coating compositions of the invention can be subjected to freeze-thaw cycles using ASTM method D2243-82 or ASTM D2243-95 without coagulation.

In one preferred embodiment of the invention, the aqueous coating composition is a latex paint composition comprising at least one latex polymer derived from at least one acrylic monomer selected from the group consisting of acrylic acid, acrylic acid esters, methacrylic acid, and methacrylic acid esters and at least one compound of the formula I or II; at least one pigment and water. As mentioned above, the at least one latex polymer can be a pure acrylic, a styrene acrylic, a vinyl acrylic or an acrylated ethylene vinyl acetate copolymer.

The present invention further includes a method of preparing an aqueous coating composition by mixing together at least one latex polymer derived from at least one monomer and mixed with a compound of the formula I or II and at least one pigment. Typically, the latex polymer is in the form of a latex polymer dispersion. The additives discussed above can be added in any suitable order to the latex polymer, the pigment, or combinations thereof, to provide these additives in the aqueous coating composition. In the case of paint formulations, the aqueous coating composition typically has a pH of from 7 to 10.

In this particular invention, the additives were added to the paint after it was formulated and were mixed in at levels of 0.05%-5.0% using non-aggressive blade mixing.

The most preferred compounds were found to be (see the introduction to the example table for the key to the abbreviations)

POE(16)DSP reacted with one mole of AGE
POE(16)DSP reacted with two moles of AGE
POE(10)TSP reacted with one mole of AGE
POE(10)TSP reacted with one mole of AGE and then sulfated
POE(10)TSP reacted with two moles of AGE
POE(10)TSP reacted with two moles of AGE and then sulfated
POE(10) beta naphthol
DDBSA formulated with TEA, water and a water soluble reverse block copolymer.

Where the abbreviations stand for: F/T=Freeze/thaw, O/T=Open time, DSP=distyrenated phenol, TSP=tristyrenated phenol, POE=polyoxyethylene polymer chain, AGE=allyl-glycidyl ether and TCDAM=tricyclodecane monomethanol

EXAMPLES

Terms and Abbreviations

F/T=Freeze/thaw
O/T=Open time
DSP=distyrenated phenol
TSP=tristyrenated phenol
POE=polyoxyethylene polymer chain
AGE=allyl glycidyl ether
TCDAM=tricyclodecane monomethanol Test Procedure Descriptions Open-Time Determination Two stocks of water-based semi gloss latex paints were provided by Behr Paints of California. One was formulated with a standard additive to improve its open time and the other was formulated without it. The version with the additive was tested as the control for the open-time evaluations. Comparisons of the test agents were made by post-adding the agents at various percentages to aliquots of the version of the paint that was formulated without additive and then determining the open times. The post-additions were made by simple ambient mixing using an overhead mixer with a two-inch blade turning at 180 rpm.

All open-times were determined using the method outlined in ASTM method D 7488-10 and the associated method D-5608. Open-time is the length of time that flaws in a paint film can be smoothed over with a paint brush after the first coat has been applied. The test method consists of drawing down a film of paint at a certain thickness onto a Leneta contrast sheet and scratching "X" marks in the film at various points along its length. This is followed by conditioning the film and then attempting to smooth out the "X" marks at various times using a paint brush that has been presoaked in the paint. The length of time that the "X" marks can be painted smooth is noted for each additive (this is the open-time) and the longer the time, the better. As an additional check, the length of time that the raised edge of the original paint strip can the smoothed is also noted as an open time.

Freeze-Thaw Determinations:

Commercially available Martha Stewart Living White/Base 1 interior acrylic latex semi-gloss MSL3011 and Martha Stewart Living White/Base 1 interior acrylic latex semi-gloss MSL3011N paints (both having 50 g/L VOC) were found to have no freeze-thaw resistance under the conditions of ASTM method D2243-95. These paints were used interchangeably as a substrate to which the various test additives were post-added at various percentages. The freeze-thaw test consists of placing a container of several ml of the test paint mixture in a chamber at −18 C for 17 hours followed by allowing it to thaw under ambient conditions for 7 hours. A sample was deemed to pass a cycle if after freezing solid it thawed back to its original uniformity and flow characteristics. If the sample passed, the test was repeated up to a maximum of five freeze-thaw cycles.

The post-addition blends were made by adding the additives to 100 g aliquots of paint and blending the mixtures using an overhead metal blade mixer with a 2-inch blade turning at about 180 rpm under ambient conditions.

The control additive for the Freeze-Thaw tests was Rhodoline FT-100 (Rhodia) which is a commercially available agent sold as a freeze-thaw improver. The FT-100 is reported to be a tristyrenated phenol with about 10 moles of ethylene oxide reacted to it.

Synthesis of Additives to be Evaluated.

Additives 3-10 (See Table of Compositions, Below.)

The hydrophobes were added to a stainless steel autoclave at the levels shown in the table below, along with potassium hydroxide at catalytic levels (2-3 grams) and the autoclave sealed and heated to 105 C. Ethylene oxide was then added, at the levels indicated on the table, over the course of several hours. After all of the EO was consumed, the reaction mass was cooled and the catalyst neutralized with the addition of a small amount of acid.

Additives 12-17

Step one: The hydrophobes, TSP or DSP, are added at the levels shown in the table below to a stainless steel autoclave, along with allyl glycidyl ether (AGE) (also at the levels shown) and a catalytic amount of potassium hydroxide (2-3 grams) and the mix heated to 105 C. When all of the AGE was consumed, the reaction mass was cooled, and the product discharged.

Step 2: The styrenated phenol/AGE adducts from step 1 were then added to another autoclave and heated to 105 C. Ethylene oxide, at the level shown in the table below, was then added over the course of several hours. After all the EO was consumed, the reaction mass was cooled and the catalyst neutralized with the addition of a small amount of acid.

Step 3 (for Examples 15 and 17): Selected surfactants from steps 1 and 2 were sulfated with sulfamic acid and a trace amount of dicyandiamide catalyst in a glass reactor equipped with a stirrer, thermometer, and reflux condenser by heating to 120 C until the % sulfate was >90%. The products were then isolated as the ammonium salt.

Table of compositions for Additives

| Additive | Hydrophobe (equiv.)/ (% wgt) | AGE (equiv.)/ (% wgt) | EO (equiv)/ (% wgt) | Sulfamic acid (equiv.)/ (% agt) | Terminal group |
|---|---|---|---|---|---|
| (1) (Behr paint blank for O/T) | NA | NA | NA | NA | NA |
| (2) (Commercial paint with no F/T) | NA | NA | NA | NA | NA |
| (3) POE(10) TSP | TSP (1)/ (45.91%) | NA | (10)/ (53.43%) | NA | —OH |
| (4) POE(11.5) DSP | DSP (1)/ (32.92%) | NA | (11.5)/ (56.1%) | NA | —OH |
| (5) POE(20)DSP | DSP (1)/ (23.18%) | NA | (20)/ (76.6%) | | —OH |
| (6) POE(10) Beta Naphthol | Beta naphthol (1) (22.92%) | NA | (10)/ (62.93%) | NA | —OH |
| (7) POE(10)cydecanol | Cydecanol (1)/ (25.35%) | NA | (10)/ (74.43%) | NA | —OH |
| (8) POE(10)TCDAM | TCDAM (1)/ (27.27%) | NA | (10)/ (72.33%) | NA | —OH |
| (9) POE(10)4-cumylphenol | 4-cumylphenol (1)/ (32.42%) | NA | (10)/ (67.36%) | NA | —OH |
| (10) POE(10)4-tertamylphenol | 4-tertamylphenol (1)/ (27.02%) | NA | (10)/ (72.56%) | NA | —OH |
| (11) POE(16)DSP-AGE | DSP (1)/ (27.6%) | (1)/ (16.96%) | (16)/ (61.91%) | NA | —OH |
| (12) POE(15)DSP-AGE (2) | DSP (1)/ (25.8%) | (2)/ (19.5%) | (15)/ (54.68%) | NA | —OH |
| (13) POE(10)TSP -AGE | TSP (1)/ (41.06%) | (1)/ (11.6%) | (10)/ (47.09%) | NA | —OH |
| (14) POE(10)TSP-AGE Sulfated not neutralized | TSP (1)/ (37.32%) | (1)/ (10.55%) | (10)/ (42.8%) | (1)/ (8.98%) | —OSO3 |
| (15) POE(10)TSP-AGE (2) | TSP (1)/ (36.93%) | (2)/ (20.84%) | (10)/ (41.96%) | NA | —OH |
| (16) POE(10)TSP-AGE (2) Sulfated Not neutralized | TSP (1)/ (33.90%) | (2)/ (19.13%) | (10)/ (38.52%) | (1)/ (8.08%) | —OSO3— |

Table of Open-Time and Freeze-Thaw Test Results

| Additive | Additive Description | % Additive actives on Blank for Open time | Edge Time | "X" Time | Gloss 60 deg | % Additive For Freeze-Thaw | Number of cycles passed |
|---|---|---|---|---|---|---|---|
| 1 | Control paint for open time: Behr Semi gloss with standard additive (Control for open time) | ? | 4 min.. | 8 min. | 55.8 | NA | NA |
| 2 | Commercially available Rhodaline FT-100 in Martha Stewart paint (Control for Freeze-Thaw) | 0.5% | 4 min. | 6 min. | 58.1 | 0.5% | None |
| | | 1.0% | 4 min. | 8 min. | 58.7 | 1.0% | None |
| | | 1.5% | | | | 1.5% | None |
| | | 2.0% | 4 min. | 8 min. | 63.3 | 2.0% | 5 |
| | | | | | | 2.5% | 5 |
| | | | | | | 3.0% | 5 |
| 3 | POE(10) TSP | 0.5% | | | | 0.5% | None |
| | | 1.0% | | | | 1.0% | 5 |
| | | 1.5% | | | | 1.5% | 5 |
| | | 2.0% | | | | 2.0% | 5 |
| | | 2.5% | | | | 2.5% | 5 |
| | | 3.0% | | | | 3.0% | 5 |

Table of Open-Time and Freeze-Thaw Test Results (continued)

| Additive | Additive Description | % Additive actives on Blank for Open time | Edge Time | "X" Time | Gloss 60 deg | % Additive For Freeze-Thaw | Number of cycles passed |
|---|---|---|---|---|---|---|---|
| 4 | POE(11.5) DSP | 0.5% | 6 min | 8 min. | 58.6 | 0.5% | None |
|   |   | 1.0% | 6 min | 12 min | 56.5 | 1.0% | None |
|   |   | 1.5% |   |   |   | 1.5% | None |
|   |   | 2.0% | 10 min | 14 min | 60.7 | 2.0% | 5 |
| 5 | POE(20) DSP | 0.5% | 6 min | 10 min. | 58.6 | 0.5% | None |
|   |   | 1.0% | 8 min | 14 min | 56.5 | 1.0% | None |
|   |   | 1.5% |   |   |   | 1.5% | None |
|   |   | 2.0% | 10 min | 20 min | 60.7 | 2.0% | None |
|   |   | 2.5% |   |   |   | 2.5% | None |
| 6 | POE(10) Beta Naphthol | 0.5% | 4 min. | 8 min |   | 0.5% | None |
|   |   | 1.0% | 6 min. | 10 min | 59.6 | 1.0% | 4 |
|   |   | 2.0% | 10 min. | 14 min | 61.2 | 2.0% | 5 |
| 7 | POE(10)cydecanol | 0.5% | 4 min. | 6 min. | 57.2 | 0.5% | None |
|   |   | 1.0% | 4 min. | 8 min. | 58.8 | 1.0% | None |
|   |   | 1.5% |   |   |   | 1.5% | None |
|   |   | 2.0% | 6 min. | 12 min. | 60.6 | 2.0% | None |
|   |   | 2.5% |   |   |   | 2.5% | None |
| 8 | POE(10)TCDAM | 0.5% | 4 min. | 6 min. | 53.4 | 0.5% | None |
|   |   | 1.0% | 6 min. | 6 min. | 57.2 | 1.0% | None |
|   |   | 2.0% | 6 min. | 10 min. | 60.0 | 2.0% | None |
| 9 | POE(10)4-cumylphenol | 0.5% | 4 min. | 8 min. | 56.6 | 0.5% | None |
|   |   | 1.0% | 6 min. | 12 min. | 55.6 | 1.0% | None |
|   |   | 1.5% |   |   |   | 1.5% | None |
|   |   | 2.0% | 10 min. | 18 min. | 62.0 | 2.0% | None |
|   |   | 2.5% |   |   |   | 2.5% | None |
| 10 | POE(10)4-tertamylphenol | 0.5% |   |   |   | 0.5% | None |
|   |   | 1.0% | 6 min | 8 min. | 56.9 | 1.0% | None |
|   |   | 1.5% |   |   |   | 1.5% | None |
|   |   | 2.0% | 8 min. | 12 min | 59.7 | 2.0% | None |
|   |   | 2.5% |   |   |   | 2.5% | None |
| 11 | POE(16)DSP AGE | 0.5% | 6 min | 10 min | 57.3 | 0.5% | * |
|   |   | 1.0% | 6 min | 14 min | 59.2 | 1.0% | None |
|   |   | 1.5% |   |   |   | 1.5% | None |
|   |   | 2.0% | 6 min | 12 min | 57.0 | 2.0% | None |
| 12 | POE(15) DSP AGE (2) | 0.5% | 6 min | 8 min | 58.4 | 0.5% | * |
|   |   | 1.0% | 6 min | 10 min | 58.5 | 1.0% | None |
|   |   | 1.5% |   |   |   | 1.5% | None |
|   |   | 2.0% | 6 min | 10 min | 62.7 | 2.0% | 1 |
| 13 | POE(10) TSP AGE | 0.5% | 6 min | 8 min | 57.8 | 0.5% | * |
|   |   | 1.0% | 4 min | 6 min | 59.7 | 1.0% | None |
|   |   | 1.5% |   |   |   | 1.5% | 5 (#5grainy) |
|   |   | 2.0% | 4 min | 6 min | 63.9 | 2.0% | 5 |
| 14 | POE(10) TSP AGE Sulfated not neutralized | 0.5% | 6 min | 10 min | 57.9 | 0.5% |  |
|   |   | 1.0% | 6 min | 10 min | 58.7 | 1.0% | None |
|   |   | 1.5% |   |   |   | 1.5% | 1 |
|   |   | 2.0% | 4 min | 12 min | 60.5 | 2.0% | 5 |
| 15 | POE(10) TSP AGE (2) | 0.5% | 4 min | 8 min | 58.0 | 0.5% | * |
|   |   | 1.0% | 4 min | 5 min | 62.2 | 1.0% | None |
|   |   | 1.5% |   |   |   | 1.5% | 5 (#5 grainy) |
|   |   | 2.0% | 4 min | 6 min | 65.4 | 2.0% | 5 |
| 16 | POE(10) TSP AGE (2) Sulfated Not neutralized | 0.5% | 4 min | 10 min | 58.3 | 0.5% |  |
|   |   | 1.0% | 6 min | 10 min | 60.1 | 1.0% | None |
|   |   | 1.5% |   |   |   | 1.5% | 2 |
|   |   | 2.0% | 6 min | 10 min | 61.9 | 2.0% | 5 |

? Indicates that it is not known whether the commercial paint has additive or not but it is used as a control for comparison purposes.

Example I

Literature teaches that ethoxylated TSP will offer improvements in the freeze-thaw performance of water-based coating formulations. Comparing additive 3 to additive 2, we see that the internally made POE(10) TSP is an improvement over the commercial material, being stable to 5 F/T cycles at 1.0% additive as opposed to 2%.

Example II

DSP, with an Appropriate Level of Ethoxylation is as Effective as TSP as a F/T Additive.

Additive 4 shows that 2% POE(11.5) DSP is as effective as the commercial TSP derivative control of additive 2 in that they both must be present at a minimum of 2%, at which level, they both pass five cycles. This example, further, shows that POE(11.5) DSP yields an O/T performance at 0.5% additive that is equal to that of the commercial standard.

Example III

The Level of Ethoxylation is Important Both to F/T and to O/T Performance of DSP Derivatives.

Comparing additive 5 to additive 4, it is evident that excessive ethoxylation damages the freeze-thaw performance while improving the O/T.

Example IV

Derivatives of DSP and TSP Other than the Original POE Offer F/T and/or OT Performances Equivalent to Those Shown in Control Tests 1 and 2.

Additives 11 and 12 indicate that POE(16)DSP reacted with one and two AGE groups yields an O/T equal to standard of Test 1.

Additives 13 and 15, which are POE(10)TSP reacted with 1 and 2 moles of AGE respectively, show open times that are equivalent to the O/T results of the standard in Test 1 together with F/T results that are extensions compared to the results of the standard in Test 2.

Additives 14 and 16 use the sulfated versions of additives 13 and 15, respectively and indicate that sulfation yields an extension in the OT performance but a slight drop in the F/T performance.

Example V

There are Additives Other than Either DSP or TSP Derivatives that Combine Acceptable F/T and O/T Capabilities.

Additive 6 compared to additives 1 and 2 indicates that POE(10) beta naphthol causes acceptable open-times and freeze-thaws.

Example VI

Additives 7, 8, 9, and 10, indicate that POE(10) cydecanol, POE(10)TCDAM, POE(10) 4-cumylphenol and POE (10) tert-amylphenol show reasonable O/T performance, compared to the control tests 1 and 2 even though F/T performance was diminished. Again, these are non-DSP and non-TSP agents.

The contents of all references cited in the instant specifications and all cited references in each of those references are incorporated in their entirety by reference herein as if those references were denoted in the text.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

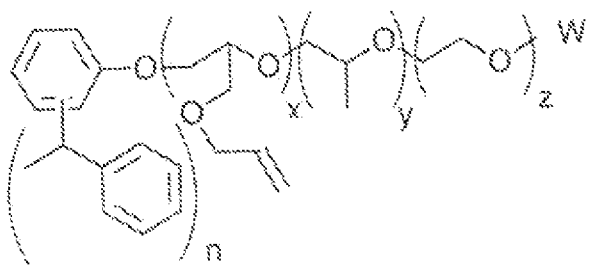

The invention claimed is:

1. A coating composition comprising: (a) at least one latex polymer; (b) water; and (c) at least one open time and freeze-thaw additive in an amount effective to increase the open time and freeze thaw properties of the coating composition, the additive having the structural formula

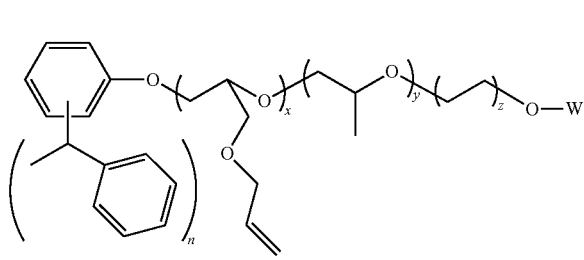

where n=1-3, x=1-5, y=0-10, z=5-40, W is selected from the group consisting of hydrogen and $Z^-M^+$ where $Z^-$ is selected from the group consisting of $SO_3^-$ and $PO_3^{2-}$, and $M^+$ is selected from the group consisting of $Na^+$, $K^+$, $NH_4^+$, or an alkanolamine; and wherein the additive is present in an amount greater than about 0.5% by weight of the polymer.

2. The coating composition of claim 1 wherein said x=1-3.

3. The coating composition of claim 1 wherein said x=1-2.

4. The coating composition of claim 1 wherein said effective amount is 0.5 to 5.0 wt %.

5. The coating composition of claim 1 having a pH of 7 to 10.

6. The coating composition of claim 1 further comprising a pigment.

7. The coating composition of claim 1 wherein said latex polymer is selected from the group consisting of styrene acrylic, vinyl acrylic and acrylated ethylene vinyl acetate copolymer.

8. The coating composition of claim 1 wherein said latex polymer comprises at least one monomer selected from the group consisting of acrylic acid, acrylic acid ester, methacrylic acid and methacrylic acid ester.

* * * * *

UNITED STATES PATENT AND TRADEMARK OFFICE
CERTIFICATE OF CORRECTION

Page 1 of 4

PATENT NO. : 9,644,108 B2
APPLICATION NO. : 15/093355
DATED : May 9, 2017
INVENTOR(S) : Charles F. Palmer, Jr., Lester Arnold Haney and Calvin M. Wicker, Jr.

It is certified that error appears in the above-identified patent and that said Letters Patent is hereby corrected as shown below:

In the Specification

At Column 4 Lines 35-44 replace the structure:

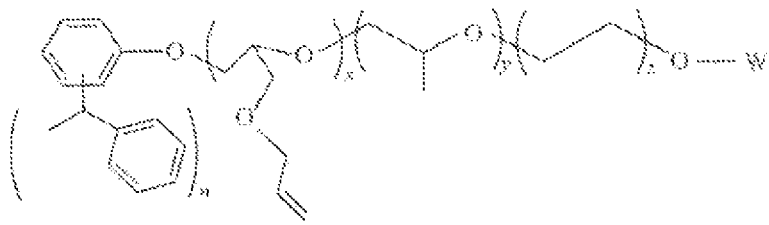

With:

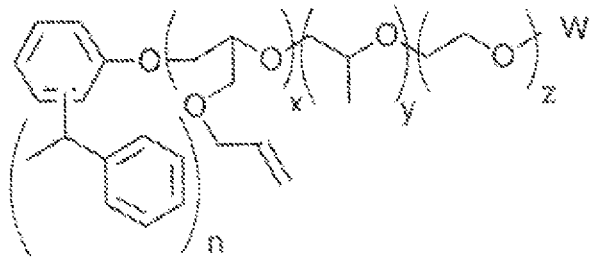

At Column 5 Lines 32-40 replace the structure:

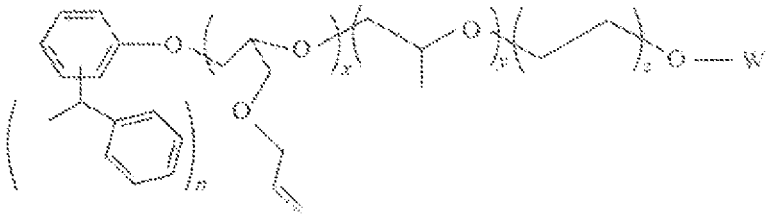

Signed and Sealed this
Twenty-second Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,644,108 B2

With:

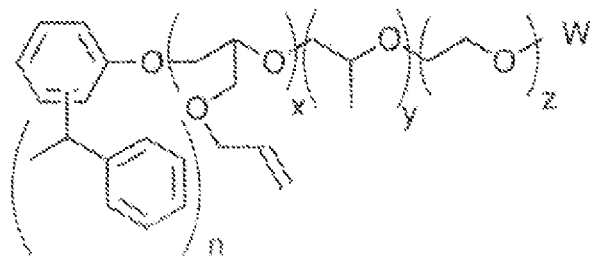

At Column 5 Line 60 to Column 6 Line 23 replace:

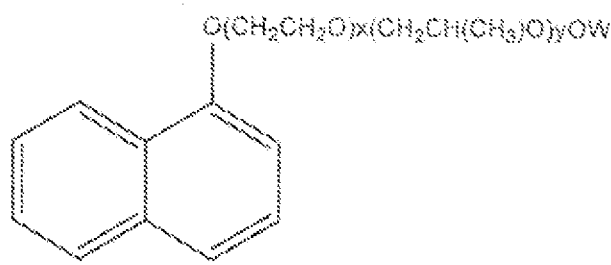

POE 10 β-naphthol

4-cumylphenol 4-tert-amylphenol

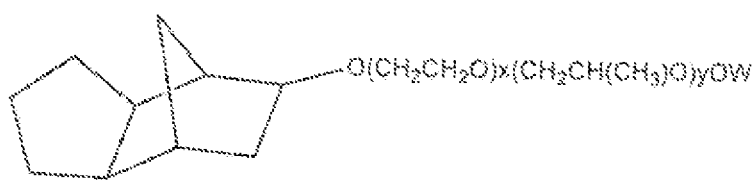

Cydenanol

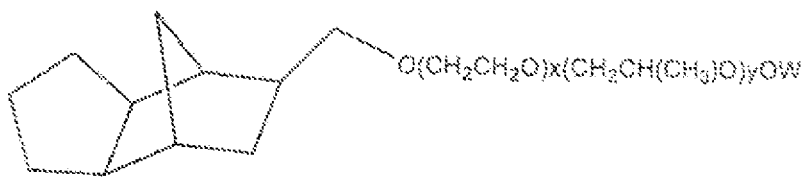

Tricyclodecyl methanol (TCDM alcohol)

With:
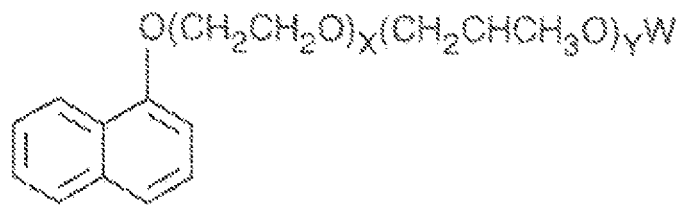
POE 10 β-naphthol
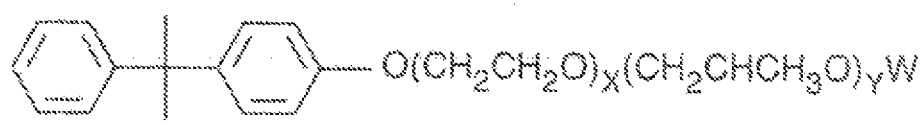
4-cumylphenol
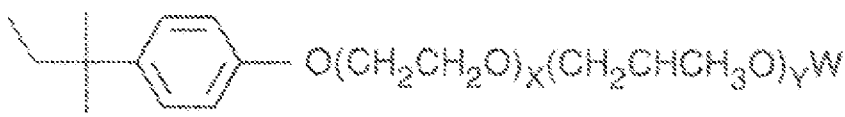
4-tert-amylphenol
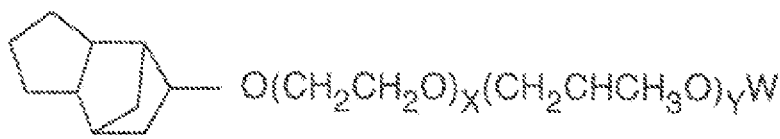
Cyclecanol
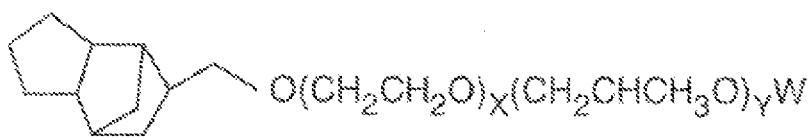
Tricyclodecyl methanol (TCDM alcohol)

CERTIFICATE OF CORRECTION (continued)
U.S. Pat. No. 9,644,108 B2

In the Claims

In Claim 1 at Column 14 Lines 26-35 replace the structure:

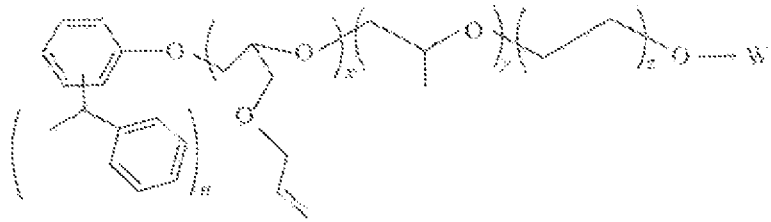

With: